(12) United States Patent
Sultan et al.

(10) Patent No.: US 7,468,673 B2
(45) Date of Patent: Dec. 23, 2008

(54) SYSTEM AND METHOD FOR DETERMINING WHETHER A VEHICLE OPERATOR HAS AN IMPAIRED COGNITIVE STATE

(75) Inventors: Michel F. Sultan, Troy, MI (US); David K. Lambert, Sterling Heights, MI (US); Laci J. Jalics, Ray, MI (US); Dale L. Partin, Ray, MI (US); Harry Zhang, Carmel, IN (US); Gerald J. Witt, Carmel, IN (US)

(73) Assignee: Delphi Technologies, Inc., Troy, MI (US)

( * ) Notice: Subject to any disclaimer, the term of this patent is extended or adjusted under 35 U.S.C. 154(b) by 364 days.

(21) Appl. No.: 11/473,625

(22) Filed: Jun. 23, 2006

(65) Prior Publication Data

US 2007/0296601 A1   Dec. 27, 2007

(51) Int. Cl.
*G08B 23/00* (2006.01)
(52) U.S. Cl. ........................... 340/576; 340/439
(58) Field of Classification Search ............ 340/576, 340/575, 471, 438, 439; 180/271, 272
See application file for complete search history.

(56) References Cited

U.S. PATENT DOCUMENTS

| | | | | |
|---|---|---|---|---|
| 6,262,657 | B1 * | 7/2001 | Okuda et al. | 340/439 |
| 6,734,799 | B2 * | 5/2004 | Munch | 340/576 |
| 6,995,663 | B2 * | 2/2006 | Geisler et al. | 340/439 |
| 6,998,972 | B2 * | 2/2006 | Geisler et al. | 340/439 |
| 2007/0290867 | A1 * | 12/2007 | Kuramori et al. | 340/576 |

OTHER PUBLICATIONS

"Innovative Fatigue Management Approach in the Trucking Industry" by Anneke Heitmann, Rainer Guttkuhn, Dean Croke, Martin Moore-Ede, Proceedings of the Third Internationals Driving Symposium on Human Factors in Driver Assessment, Training and Vehicle Design, pp. 271-277, Jun. 23, 2006.

"Circadian Alertness Simulator for Fatigue Risk Assessment in Transportation: Application to Reduce Frequency and Severity of Truck Accidents" by Martin Moore-Ede, Anneke Heitmann, Rainer Guttkuhn, Udo Trutschel, Acacia Aguirre, and Dean Croke of the Aviation, Space, and Environmental Medicine vol. 75, No. 3, Section II, pp. A107-A118.

(Continued)

*Primary Examiner*—John A Tweel, Jr.
(74) *Attorney, Agent, or Firm*—Paul L. Marshall

(57) ABSTRACT

A system and a method for determining whether an operator of a vehicle has an impaired cognitive state are provided. The method includes determining an intoxication indication value indicative of whether the operator is intoxicated, utilizing a controller. The method further includes determining a drowsiness indication value indicative of whether the operator is drowsy, utilizing the controller. The method further includes determining a fatigue indication value indicative of whether the operator is fatigued, utilizing the controller. The method further includes determining a cognitively impaired indication value based on at least one of the intoxication indication value, the drowsiness indication value, and the fatigue indication value. The method further includes generating a signal indicating that the operator is cognitively impaired when the cognitively impaired indication value is greater than a threshold cognitively impaired indication value, utilizing the controller.

37 Claims, 10 Drawing Sheets

OTHER PUBLICATIONS

"Fatigue Models for Applied Research in Warfighting" by Steven R. Hursh, Daniel P. Redmond, Michael L. Johnson, David R. Thorne, Gregory Belenky, Thomas J. Balkin, William F. Storm, James C. Miller, and Douglas R. Eddy of the Aviation, Space, and Environmental Medicine, vol. 75, No. 3, Section II, pp. A44-A53, Mar. 2004.

U.S. Appl. No. 10/348,496, filed Jan. 21, 2003 "Ethyl Alcohol Sensor and Method of Use".

U.S. Appl. No. 11/033,677, filed Jan. 12, 2005 "Chemical Vapor Sensor".

U.S. Appl. No. 11/033,703, filed Jan. 12, 2005 "Chemical Vapor Sensor Having and Active and a Passive Measurement Mode".

U.S. Appl. No. 11/243,556, filed Oct. 5, 2005 "Tracer to Compensate for Environmental Variations that Influence a Chemical Vapor Sensor Measurement".

* cited by examiner

140
- WORK
- HOSPITAL
- CLINIC
- DAY CARE
- CHURCH
- SYNAGOGUE
- TEMPLE
- MOSQUE
- MOVIE THEATRE
- ELEMENTARY SCHOOL
- MIDDLE SCHOOL
- DEALERSHIP
- BUSINESS
- DEPT. STORE
- GAS STATION
- GYM
- HAIR DRESSER
- BARBER SHOP
- COFFEE SHOP
- PLANT
- GOV BUILDING
- FIRE STATION
- POLICE STATION
- CEMETERY

142
- HOME
- HOUSING ZONE
- GROCERY STORE
- RESTAURANT
- THEATRE
- MALL
- DORM
- HOTEL
- AIRPORT
- HIGH SCHOOL
- COLLEGE
- REST AREA
- PARK, BEACH

144
- BAR
- CASINO
- BANQUET HALL
- LIQUOR STORE
- STADIUM

*FIG. 10*

SYSTEM AND METHOD FOR DETERMINING WHETHER A VEHICLE OPERATOR HAS AN IMPAIRED COGNITIVE STATE

TECHNICAL FIELD

The present application relates to a system and a method for determining whether a vehicle operator has an impaired cognitive state.

BACKGROUND

Systems have been proposed to minimize vehicle accidents due to cognitively impaired vehicle operators. One system includes use of a vehicle ignition locking mechanism when the vehicle operator is cognitively impaired to prevent the operator from starting the vehicle. Another system requires that the vehicle operator perform a test before attempting to operate the vehicle. A disadvantage with these systems is that vehicle operators consider the systems too intrusive on their freedom to operate the vehicle.

Accordingly, there is a need to provide a system and a method for determining whether a vehicle operator has an impaired cognitive state, wherein the determination is made with minimal participation of the operator and minimal intrusion on the operator's freedom to operate the vehicle.

SUMMARY OF THE INVENTION

A method for determining whether an operator of a vehicle is intoxicated in accordance with an exemplary embodiment is provided. The method includes generating a first signal indicative of a first location of the vehicle at a first time, utilizing a global positioning system device, when a vehicle ignition switch is in a predetermined operating position. The method further includes determining a location classification associated with the first location of the vehicle based on the first signal, utilizing a controller. The method further includes determining whether the operator is intoxicated based on the location classification and a time duration value indicative of the vehicle being at the first location, utilizing the controller. The method further includes generating a second signal when the operator is intoxicated, utilizing the controller.

A system for determining whether an operator of a vehicle is intoxicated in accordance with another exemplary embodiment is provided. The system includes a global positioning system device configured to generate a first signal indicative of a location of the vehicle at a first time, when a vehicle ignition switch is in a predetermined operating position. The system further includes a controller operably communicating with the global positioning system device. The controller is configured to determine whether the operator is intoxicated based on a location classification associated with the location of the vehicle based on the first signal and a time duration value indicative of the vehicle being at the location. The controller is further configured to generate a second signal when the operator is intoxicated.

A method for determining whether an operator of a vehicle is drowsy in accordance with another exemplary embodiment is provided. The method includes generating a first signal indicative of a first location of the vehicle at a first time, utilizing a global positioning system device, when a vehicle ignition switch is in a predetermined operating position. The method further includes determining a drowsiness indication value utilizing a controller based on the first signal and a time duration value indicative of the vehicle being at the first location, and if the drowsiness indication value is greater than a threshold drowsiness indication value, then generating a second signal indicating that the operator is drowsy at the first time.

A system for determining whether an operator of a vehicle is drowsy in accordance with another exemplary embodiment is provided. The system includes a global positioning system device configured to generate a first signal indicative of a location of the vehicle at a first time, when a vehicle ignition switch is in a predetermined operating position. The system further includes a controller operably communicating with the global positioning system device. The controller is configured to determine a drowsiness indication value based on the first signal and a time duration value indicative of the vehicle being at the location. The controller is further configured to generate a second signal indicating that the operator is drowsy at the first time if the drowsiness indication value is greater than a threshold drowsiness indication value.

A method for determining whether an operator of a vehicle is fatigued in accordance with another exemplary embodiment is provided. The method includes generating a first signal indicative of a first location of the vehicle at a first time, utilizing a global positioning system device, when a vehicle ignition switch is in a predetermined operating position. The method further includes determining a fatigue indication value utilizing a controller based on the first signal and a time duration value indicative of the vehicle being at the first location, and if the fatigue indication value is greater than a threshold fatigue indication value, then generating a second signal indicating that the operator is fatigued at the first time.

A system for determining whether an operator of a vehicle is fatigued in accordance with another exemplary embodiment is provided. The system includes a global positioning system device configured to generate a first signal indicative of a location of the vehicle at a first time, when a vehicle ignition switch is in a predetermined operating position. The system further includes a controller operably communicating with the global positioning system device. The controller is configured to determine a fatigue indication value based on the first signal and a time duration value indicative of the vehicle being at the location. The controller is further configured to generate a second signal indicating that the operator is fatigued at the first time if the fatigue indication value is greater than a threshold fatigue indication value.

A method for determining whether an operator of a vehicle has an impaired cognitive state in accordance with another exemplary embodiment is provided. The method includes determining an intoxication indication value indicative of whether the operator is intoxicated, utilizing a controller. The method further includes determining a drowsiness indication value indicative of whether the operator is drowsy, utilizing the controller. The method further includes determining a fatigue indication value indicative of whether the operator is fatigued, utilizing the controller. The method further includes determining a cognitively impaired indication value based on at least one of the intoxication indication value, the drowsiness indication value, and the fatigue indication value. The method further includes generating a signal indicating that the operator is cognitively impaired when the cognitively impaired indication value is greater than a threshold cognitively impaired indication value, utilizing the controller.

A system for determining whether an operator of a vehicle has an impaired cognitive state in accordance with another exemplary embodiment is provided. The system includes a controller configured to determine a cognitively impaired indication value based on at least one of an intoxication indication value, a drowsiness indication value, and a fatigue indication value. The controller is further configured to generate a signal indicating that the operator is cognitively impaired if the cognitively impaired indication value is greater than a threshold cognitively impaired indication value.

BRIEF DESCRIPTION OF THE DRAWINGS

FIG. 10 illustrates tables of classifications of vehicle locations utilized by the system of FIG. 1.

DETAILED DESCRIPTION OF EXEMPLARY EMBODIMENTS

Figure 1:
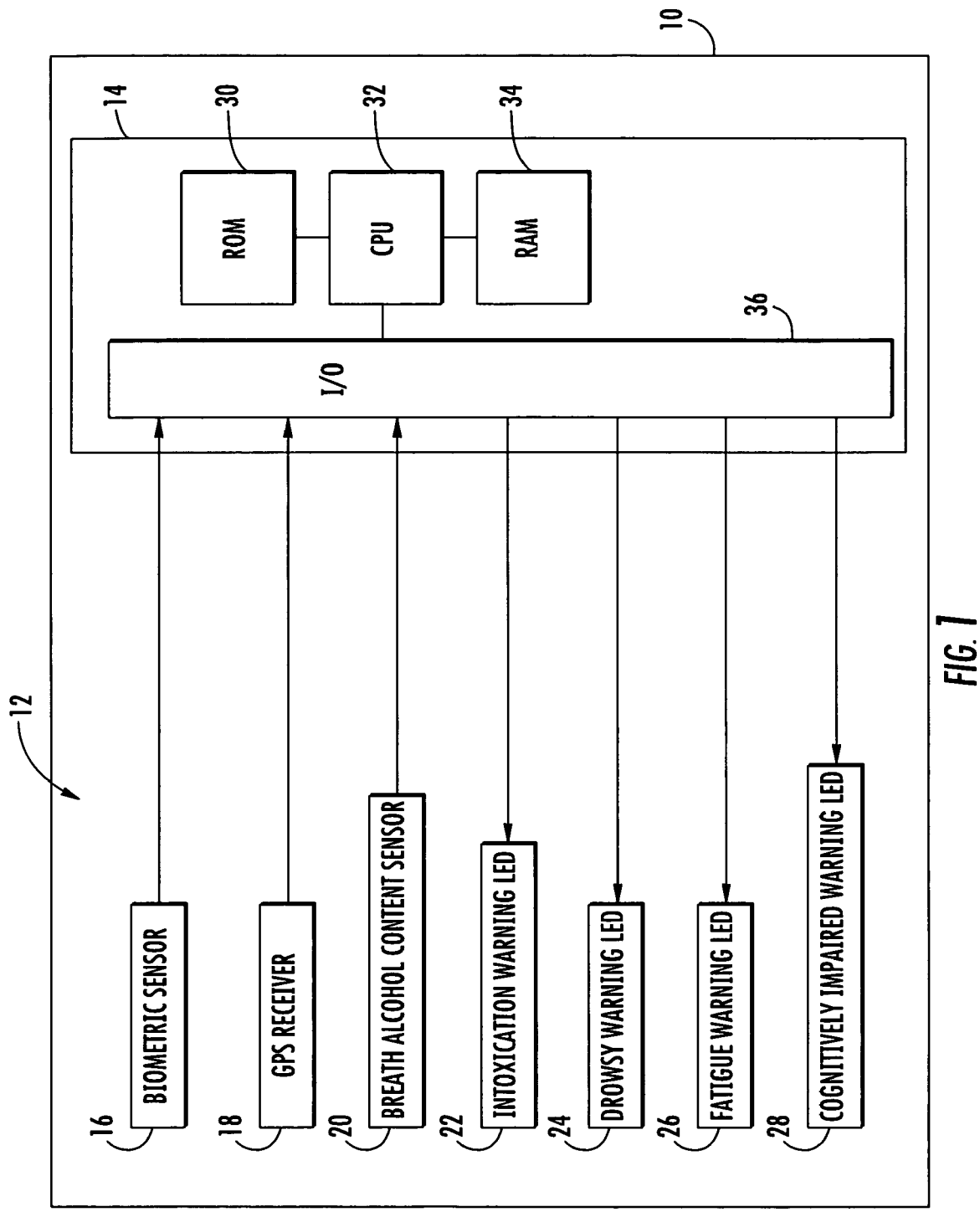
FIG. 1 is a block diagram of a system for determining whether a vehicle operator has an impaired cognitive state in accordance with an exemplary embodiment of the present invention.

Exemplary embodiments in accordance with the present invention provide an operator cognitive estimating system and method of using the same for determining a cognitive state of an operator of a vehicle. The operator cognitive estimating system includes an algorithm or method executed by a controller and configured for determining the cognitive state of the operator as related to the operator's mental capability to operate the vehicle. In one exemplary embodiment, the operator cognitive estimating system further includes a sensor for indicating a geographic location of the vehicle. In another exemplary embodiment, the operator cognitive estimating system further includes a sensor for indicating an identity of the operator.

In an exemplary embodiment, vehicle locations are classified in a manner that aids in determining the cognitive state of the operator. The algorithm is configured to assume that if the operator has driven the vehicle to a particular location, then the operator remains at that location for the same elapsed time period as the vehicle remains at that location.

For example and in one exemplary embodiment, a vehicle location, a time value that the operator starts to operate the vehicle, and an elapsed time that the vehicle remains at that location can strengthen a determination that the operator is intoxicated. For example, if the location of the vehicle is in close proximity to a tavern and the vehicle remained at that location for an extended period of time before the operator attempts to operate the vehicle at 1:00 AM on a Saturday, then it is likely that the operator consumed an amount of alcohol at the tavern sufficient to reduce the operator's cognitive ability to operate the vehicle. In another situation, if the operator has driven the vehicle from the operator's home to a location that is in close proximity to a church at 9:00 AM on a Sunday, it can be determined that very likely the operator is not intoxicated. Additionally, the determination of intoxication or non-intoxication can be strengthened by a history of substantially similar prior occurrences associated with the operator. Of course, history may include other information associated with the operator, for example a blood alcohol content associated with the operator.

In another exemplary embodiment, the vehicle location is useful in determining a drowsiness level of the operator. Drowsiness is defined as an effect upon the operator due to the operator's lack of sleep. The operator's sleep schedule and how much the operator has slept are estimated from data associated with the location of the vehicle. For example, it can be inferred that a location is the operator's home and that the operator has slept at that location from the frequency of visits to that location and elapsed times at that location. In another example, if the vehicle's location is proximate to a motel and the vehicle remained at that location for an extended amount of time, it can be inferred that the operator has slept during that time at that location. Inferences can also be made related to the benefit the operator receives from sleeping at a location. For example, it may be inferred that a passenger sleeping in a moving vehicle or the operator sleeping at a highway rest stop receives a lower benefit from the sleep compared to the benefit of sleeping at a home.

Additionally, the determination of the drowsiness level of the operator can include consideration of a local time of day. Generally, the operator's propensity to fall asleep, or level of drowsiness, is influenced by a 24-hour cycle—circadian rhythm. A similar cycle influences the benefit the operator receives from sleep. In one approximation, both the propensity of the operator to fall asleep and the benefit the operator receives from sleep have a sinusoidal variation with a 24-hour period, wherein both have a maximum value occurring at night. Given an inferred sleep schedule of the operator, estimation of a drowsiness level of the operator is known in the art. Exemplary embodiments of systems for estimating operator performance considering the influence of sleep schedule can be found in the following publications the contents of which are incorporated herein by reference thereto: Steven R. Hursh et al., Fatigue Models for Applied Research in Warfighting, 75 Aviation, Space, and Environmental Medicine, A44-A53 (2004); and Martin Moore-Ede et al., Circadian Alertness Simulator for Fatigue Risk Assessment in Transportation: Application to Reduce Frequency and Severity of Truck Accidents, ibid., A107-A118 (2004).

In another exemplary embodiment, the vehicle location is useful in determining a fatigue level of the operator. Fatigue is defined as an effect upon the operator due to work performed by the operator, wherein work includes physical and mental effort performed by the operator, including operating the vehicle. The operator's fatigue level is determined from the operator's inferred work intensity and work schedule based on the operator's operation of the vehicle. In one application, a determination of a fatigue level of the operator is based on the vehicle location, a time value that the operator starts to operate the vehicle, and a history of prior occurrences associated with the operator. A location of employment may be inferred and categorized by its business nature or simply from an amount of time the operator and the vehicle remain at that location. For example, a theatre is likely to be an operator's location of employment when the vehicle and the operator remain at a location in close proximity to the theatre for an extended time each day, for several days on a weekly basis. The operator is likely to experience a level of fatigue when leaving the theatre after an extended time of working at the theatre. In contrast, an operator who occasionally is at that location for a short amount of time is inferred to be a customer of the theatre who experiences a lower level of fatigue when leaving the theatre. In another application, a level of operator fatigue is determined at least in part due to driving conditions. For example, it is inferred that the operator experiences more fatigue over time driving in congested traffic conditions, e.g. rush hour, stop-and-go traffic, etc., compared to driving at constant speeds without traffic congestion.

In an exemplary embodiment, the controller executes the algorithm for determining the cognitive state of the operator when a vehicle ignition is in a predetermined operating position. The algorithm continues to operate while the operator operates the vehicle, thereby providing an on-going estimate of the vehicle operator's cognitive ability to operate the vehicle. For example, the controller executes the algorithm when the vehicle ignition is in a position to start the vehicle's engine or when the vehicle's transmission is engaged in a mode other than a parked operational mode.

In an exemplary embodiment, the operator cognitive estimating system further includes a controller configured to update a memory with data associated with the vehicle's location, vehicle location attributes or classifications, the operator's operation of the vehicle and any data associated with the operator. The memory can be updated by any known method such as manually via use of an input device, updated via sensor signals or by wireless methods. The data stored in the memory provides historical data for use by the algorithm at a future time when the algorithm is executed. Additionally, it is intended that the controller be further configured to allow for the implementation of an updated algorithm for determining the cognitive state of the operator. In non-limiting examples, the controller allows the algorithm to be updated or replaced for new sensor technology or for information associated with the operator and operation of the vehicle.

In an exemplary embodiment, the controller is further configured to activate a counter-measure in response to the operator cognitive estimating system determining that the operator has a cognitively impaired state that exceeds a predetermined threshold cognitively impaired state. In an exemplary embodiment, the counter-measure provides a visual or audible warning or notification to the operator that further operation of the vehicle by the operator is undesirable due to the operator's cognitively impaired state. In an alternative exemplary embodiment, the counter-measure is notification of a third party and/or temporary disablement of a portion of the vehicle until the operator's cognitive impaired state is eliminated or when the operator cognitive estimating system identifies another operator of the vehicle.

In an exemplary embodiment disclosed herein, the operator cognitive estimating system determines the cognitive state of the operator based on an intoxication indication value, a drowsiness indication value, a fatigue indication value, and a cognitively impaired value. In another exemplary embodiment, the operator cognitive estimating system determines the operator's cognitive state based on any combination of the intoxication indication value, the drowsiness indication value, the fatigue indication value, and the cognitively impaired value. Additionally, and in an alternative exemplary embodiment, the operator cognitive estimating system determines the cognitive state of the operator utilizing a plurality of vehicle operational sensors that provide signals to the controller for use with the algorithm in the determining the cognitive state of the operator.

Referring now to FIG. 1, a vehicle 10 having an operator cognitive state estimating system 12 in accordance with an exemplary embodiment of the present invention is illustrated. Operator cognitive state estimating system 12 is provided to estimate a cognitive state of the operator of vehicle 10. In an exemplary embodiment, system 12 includes a controller 14, a biometric sensor 16, a global positioning system (GPS) device 18, a breath alcohol content sensor 20, an intoxication warning light-emitting diode (LED) 22, a drowsy warning LED 24, a fatigue warning LED 26, and a cognitively impaired warning LED 28.

Controller 14 is configured to utilize an algorithm for determining the cognitive state of the operator. Controller 14 is further configured to receive and store data associated with vehicle 10 and the operator's operation thereof. For example, controller 14 is configured to determine a cognitive state of the operator based upon signals received from biometric sensor 16, GPS device 18, and breath alcohol content sensor 20.

Controller 14 is further configured to activate intoxication warning LED 22, drowsy warning LED 24, fatigue warning LED 26, and cognitively impaired warning LED 28, thereby providing visual notice to the operator of an undesirable cognitive state of the operator as related to operation of the vehicle.

In an exemplary embodiment, controller 14 includes a read-only memory (ROM) 30, a central processing unit (CPU) 32, a volatile memory such as a random access memory (RAM) 34, and an input/output (I/O) interface 36. CPU 32 operably communicates with ROM 30, RAM 34, and I/O interface 36. Any number of known memory and input/output devices may be utilized by controller 14 for storing data, sending and receiving signals.

Biometric sensor 16 is provided to confirm an identity of the vehicle operator. In an exemplary embodiment, the biometric sensor is a fingerprint detecting device. In another embodiment, biometric sensor 16 is an image recognition device, for example, a face or eye recognition device.

GPS device 18 is provided to determine a geographic location of the vehicle. In an exemplary embodiment, GPS device 18 is a GPS receiver that determines a geographic location based on at least three GPS signals received from three geosynchronous satellites.

Breath alcohol content sensor 20 is provided to estimate a blood alcohol concentration of the operator. In an exemplary embodiment, breath alcohol content sensor 20 is a passive sensor configured to estimate a blood alcohol content value of the operator without the operator's participation other than the operator's normal breathing. In another exemplary embodiment, breath alcohol content sensor 20 is an active sensor that requires the operator's participation in order for the breath alcohol content sensor to obtain a breath alcohol content value from the operator. Exemplary embodiments of systems for estimating an intoxicated condition of a vehicle operator can be found in the following U.S. Patent Applications the contents of which are incorporated herein by reference thereto: "ETHYL ALCOHOL SENSOR AND METHOD OF USE," U.S. Ser. No. 10/348,496 filed Jan. 21, 2003; "CHEMICAL VAPOR SENSOR," U.S. Ser. No. 11/033,677 filed Jan. 12, 2005; "CHEMICAL VAPOR SENSOR HAVING AN ACTIVE AND A PASSIVE MEASUREMENT MODE," U.S. Ser. No. 11/033,703 filed Jan. 12, 2005; and "TRACER TO COMPENSATE FOR ENVIRONMENTAL VARIATIONS THAT INFLUENCE A CHEMICAL VAPOR SENSOR MEASUREMENT," U.S. Ser. No. 11/243,556 filed Oct. 5, 2005.

Figure 2:
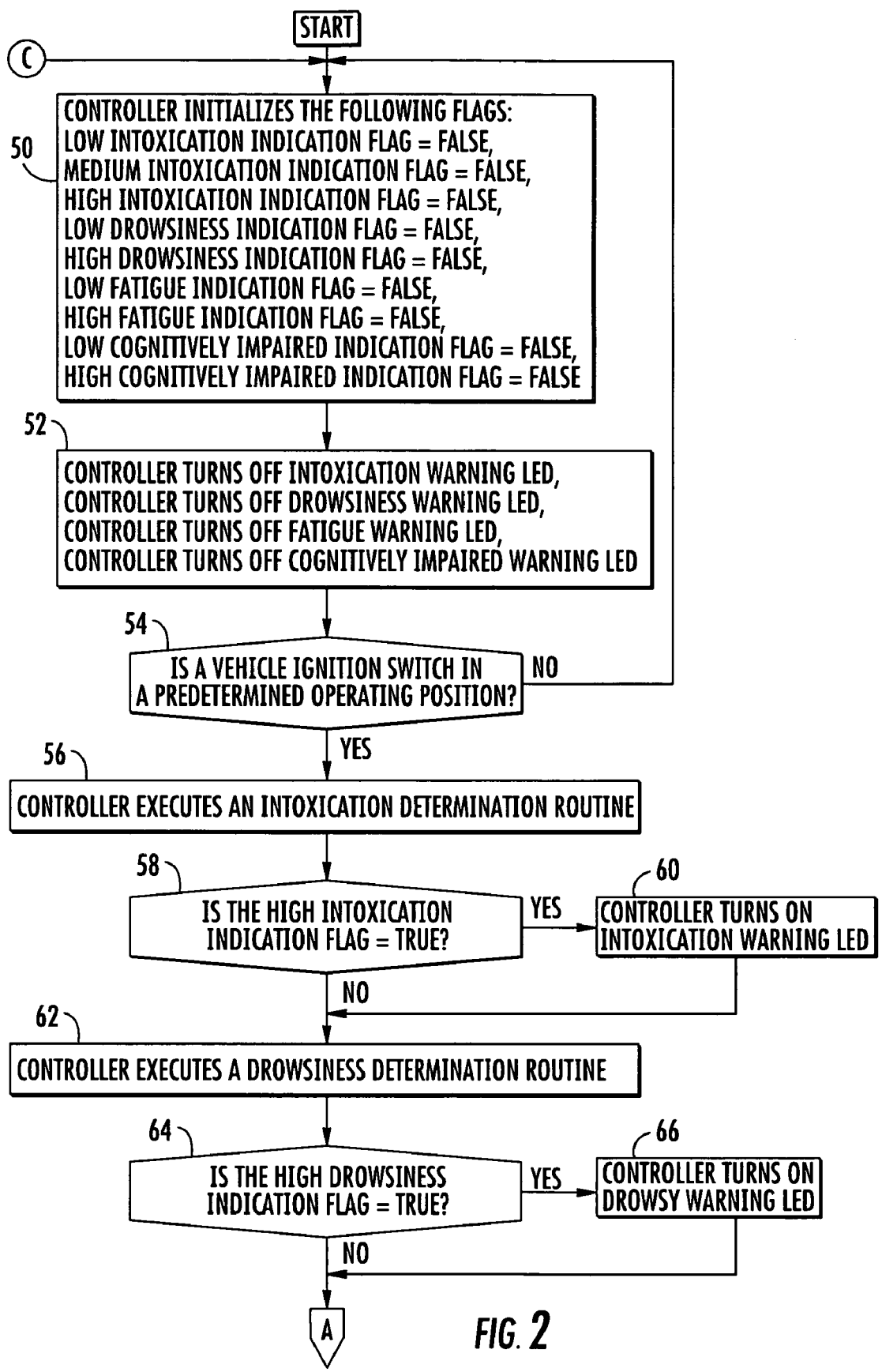
FIGS. 2-9 are flowcharts of a method for determining whether a vehicle operator has an impaired cognitive state in accordance with another exemplary embodiment of the present invention.
Figure 3:
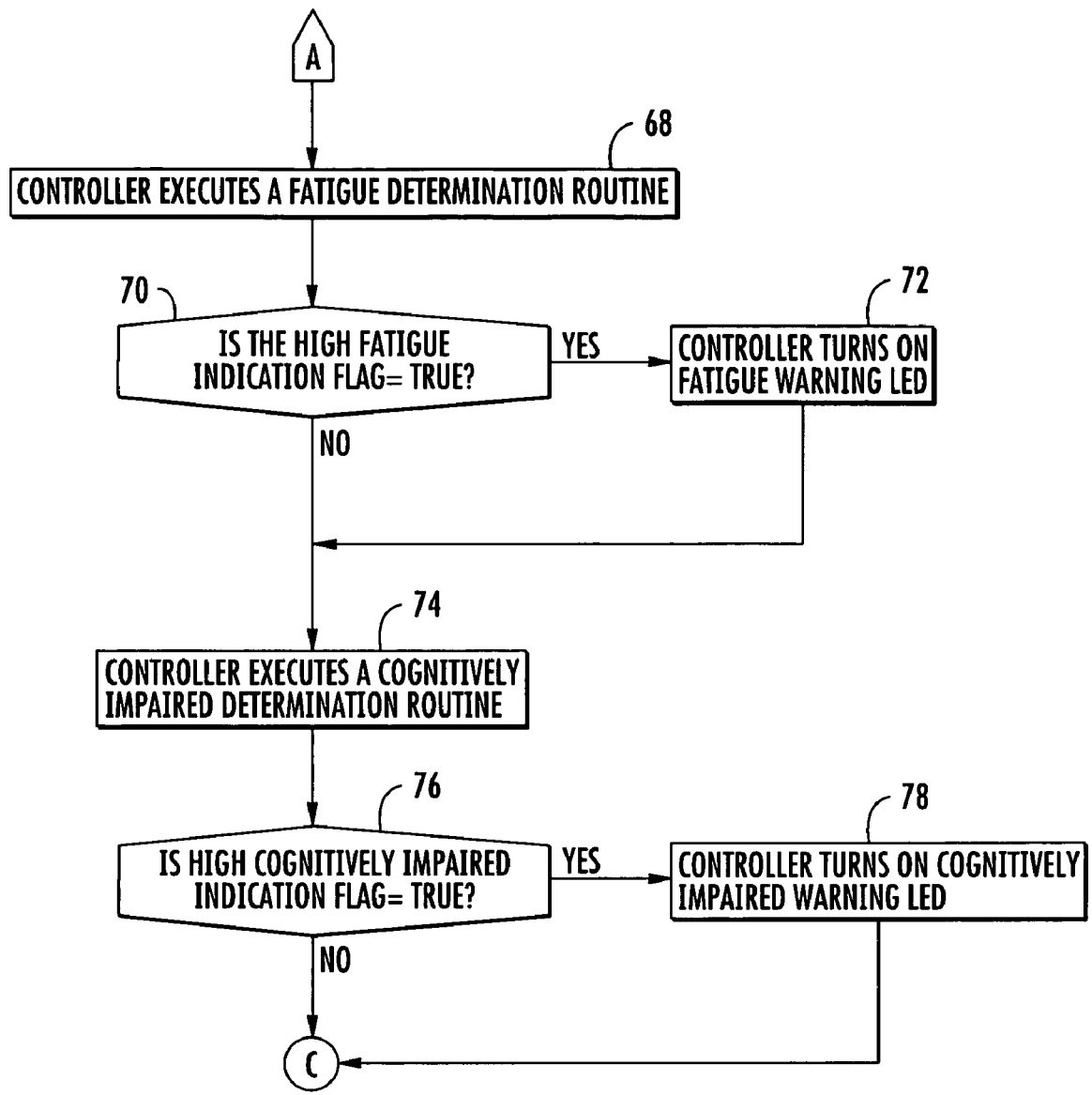

Referring now to FIGS. 2 and 3, a method for determining a vehicle operator's cognitive state in accordance with an exemplary embodiment is illustrated. The method includes an intoxication determination routine, a drowsiness determination routine, a fatigue determination routine, and a cognitively impaired determination routine.

At step 50, controller 14 initializes the following flags by setting each of them equal to "false": a low intoxication indication flag, a medium intoxication indication flag, a high intoxication indication flag, a low drowsiness indication flag, a high drowsiness indication flag, a low fatigue indication flag, a high fatigue indication flag, a low cognitively impaired indication flag, and a high cognitively impaired indication flag.

At step 52, controller 14 turns off intoxication warning LED 22, drowsy warning LED 24, fatigue warning LED 26, and cognitively impaired warning LED 28.

At step 54, controller 14 makes a determination as to whether a vehicle ignition switch is in a predetermined operating position. For example, controller 14 determines if the vehicle ignition switch is in an operating position that allows the operator to start the vehicle's engine and/or engage the vehicle's transmission. If the value of step 54 equals "yes," then the method proceeds to step 56. Otherwise, the method returns to step 50.

At step 56, controller 14 executes the intoxication determination routine. Controller 14 utilizes the intoxication determination routine, illustrated in FIGS. 4-6, to determine whether the operator is intoxicated. A detailed explanation of the intoxication determination routine is provided later herein.

At step 58, controller 14 makes a determination as to whether the intoxication determination routine has set the high intoxication indication flag equal to "true." If the value of step 58 equals "yes," then the method proceeds to step 60. Otherwise, the method proceeds to step 62.

At step 62, controller 14 executes the drowsiness determination routine. Controller 14 utilizes the drowsiness determination routine, illustrated in FIG. 7, to determine whether the operator is drowsy. A detailed explanation of the drowsiness determination routine is provided later herein.

At step 64, controller 14 makes a determination as to whether the drowsiness determination routine has set the high drowsiness indication flag equal to "true." If the value of step 64 equals "yes," then the method proceeds to step 66. Otherwise, the method proceeds to step 68.

At step 68, controller 14 executes the fatigue determination routine. Controller 14 utilizes the fatigue determination routine, illustrated in FIG. 8, to determine whether the operator is fatigued. A detailed explanation of the fatigue determination routine is provided later herein.

At step 70, controller 14 makes a determination as to whether the fatigue determination routine has set the high fatigue indication flag equal to "true." If the value of step 70 equals "yes," then the method proceeds to step 72. Otherwise, the method proceeds to step 74.

At step 74, controller 14 executes the cognitively impaired determination routine. Controller 14 utilizes the cognitively impaired determination routine, illustrated in FIG. 9, to determine whether the operator is cognitively impaired. A detailed explanation of the cognitively impaired determination routine is provided later herein.

At step 76, controller 14 makes a determination as to whether the cognitively impaired determination routine has set the high cognitively impaired indication flag equal to "true." If the value of step 76 equals "yes," then the method proceeds to step 78. Otherwise, the method returns to step 50 to repeat the method for determining the cognitive state of the operator.

Figure 4:
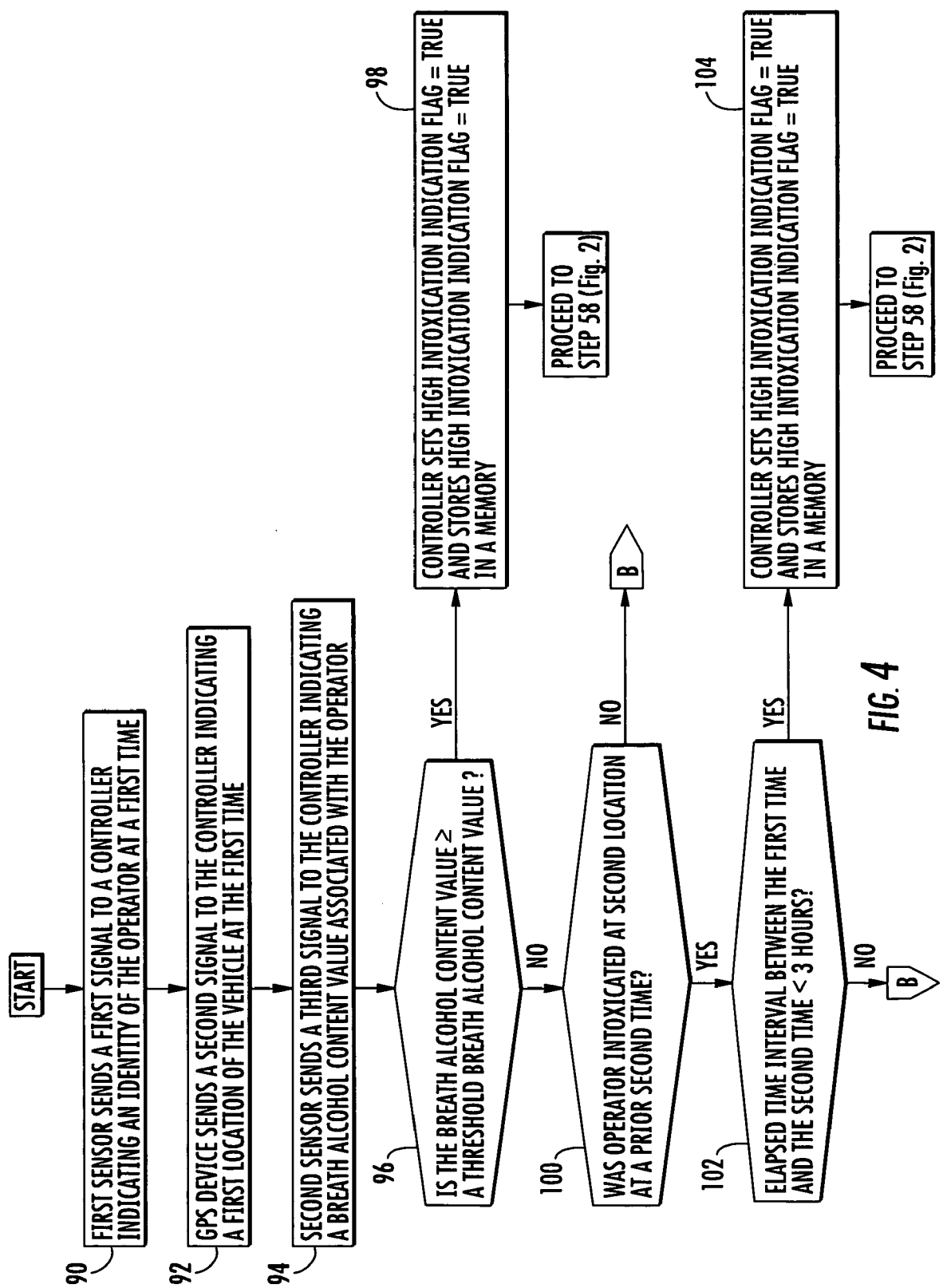
Figure 5:
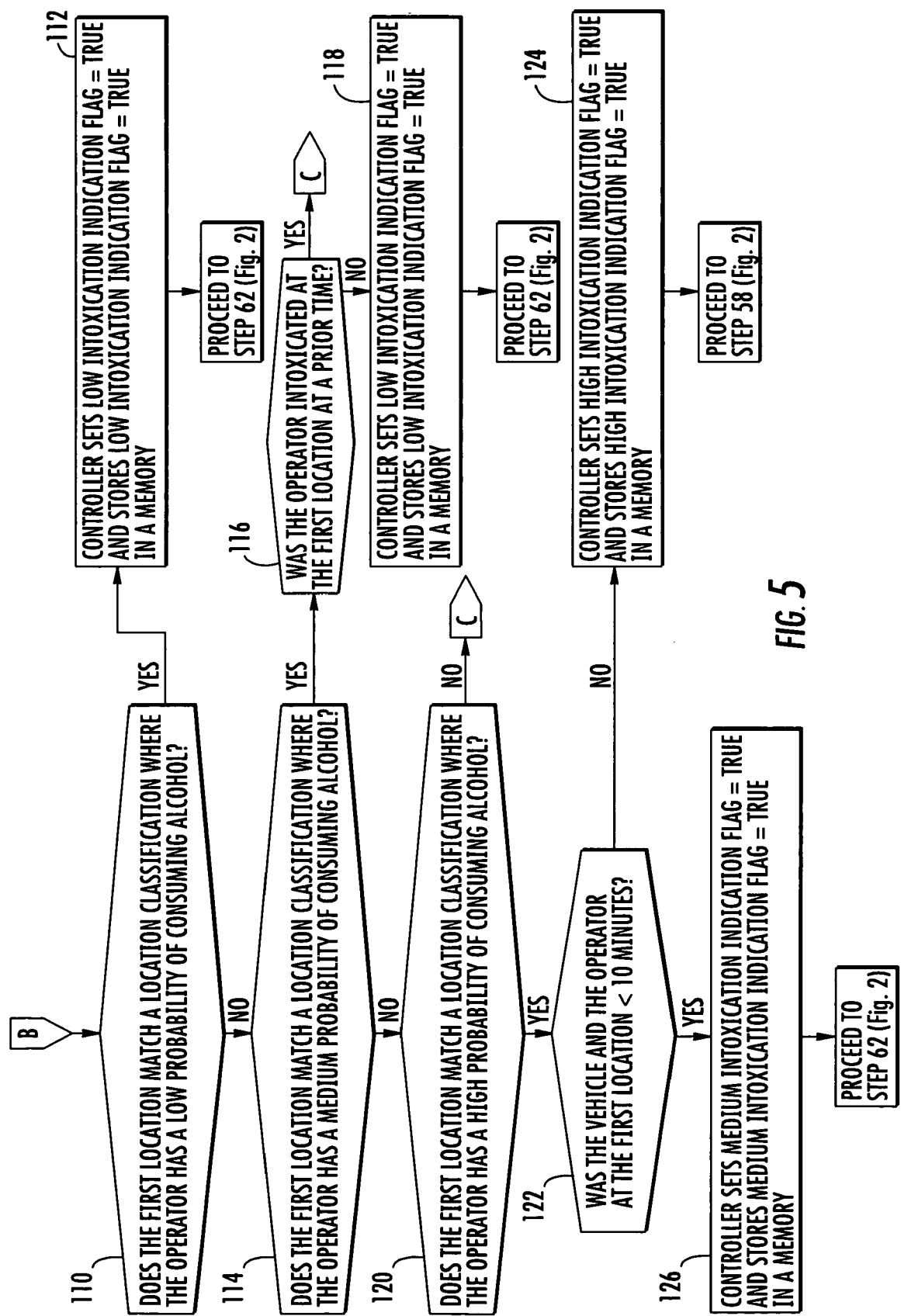
Figure 6:
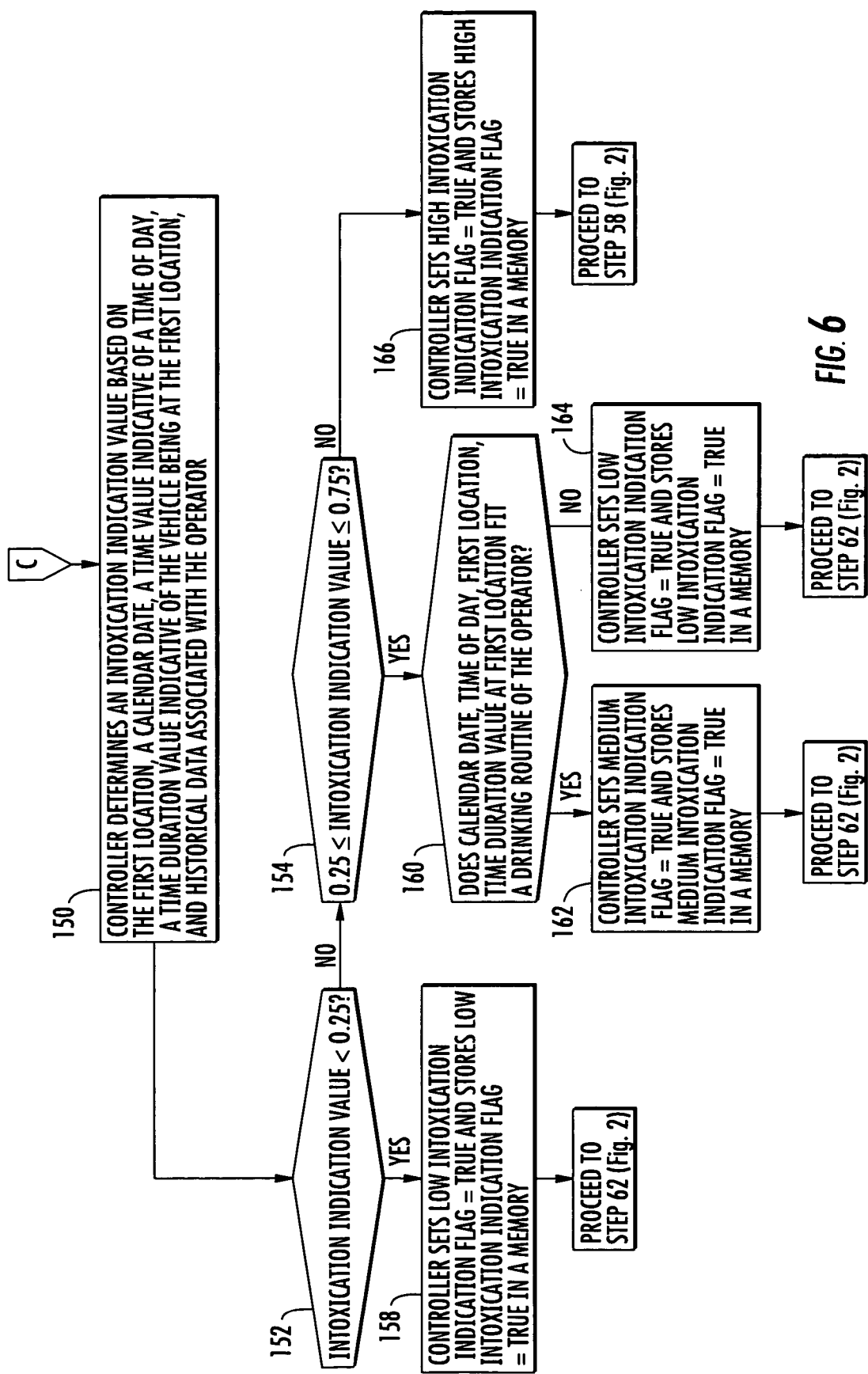

Referring now to FIGS. 4-6 the intoxication determination routine will now be explained. In one exemplary embodiment, the intoxication determination routine determines whether the operator is intoxicated based on a vehicle location and an amount of time the vehicle has been at that location. In another exemplary embodiment, the intoxication determination routine determines whether the operator is intoxicated based on additional data, for example data received from additional sensors and historical data.

At step 90, biometric sensor 16 sends a first signal to controller 14 indicating an identity of the operator at a first time. For example, biometric sensor 16 sends the first signal to controller 14 when the operator places the vehicle ignition switch in the predetermined operating position. In an exemplary embodiment, if the identity of the operator is the same identity of the operator at a prior time, controller 14 retrieves historical data associated with the operator's prior operation of the vehicle from a memory for use with the intoxication determination routine.

At step 92, GPS device 18 sends a second signal to controller 14 indicating a first location of the vehicle at the first time.

At step 94, breath alcohol content sensor 20 sends a third signal to controller 14 indicating a breath alcohol content value associated with the operator.

At step 96, controller 14 makes a determination as to whether the breath alcohol content value is greater than or equal to a threshold breath alcohol content value. If the value of step 96 equals "yes," then the method proceeds to step 98. Otherwise, the method step proceeds to step 100.

At step 98, controller 14 sets the high intoxication indication flag equal to "true" and stores the high intoxication indication flag in a memory. It should be noted that the high intoxication indication flag is considered historical data that is accessible by controller 14 when the operator is driving the vehicle at a later time. After step 98, the method proceeds to step 58.

At step 100, controller 14 makes a determination as to whether the operator was intoxicated at a second location at a prior second time. If the value of step 100 equals "no," then the method proceeds to step 110 wherein controller 14 further considers attributes of the first location in determining if the operator is intoxicated. Otherwise, the method proceeds to step 102.

At step 102, controller 14 makes a determination as to whether an elapsed time interval between the first time and the second time is less than a threshold time value. For example, is the elapsed time interval between the first time and the second time less than three hours? If the value of step 102 equals "yes," then the method proceeds to step 104. Otherwise, the method proceeds to step 110.

At step 104, controller 14 sets the high intoxication indication flag equal to "true" and stores the high intoxication indication flag in a memory. After step 104, the method then proceeds to step 58.

Referring now to FIGS. 5 and 10, the intoxication determination routine considers attributes of the vehicle's location in determining if the operator is intoxicated. For example and referring to FIG. 10, three vehicle location classifications 140, 142 and 144 are illustrated. Vehicle location classification 140 lists examples of locations where the operator generally has a low probability of consuming alcohol. Vehicle location classification 142 lists examples of locations where the operator generally has a medium probability of consuming alcohol. Vehicle location classification 144 lists examples of locations where the operator generally has a high probability of consuming alcohol. It is contemplated that if a location is one where alcohol normally is consumed, the more likely it is over a period of time that the operator will consume an amount of alcohol that results in the operator being intoxicated to a level to reduce the operator's cognitive ability to operate the vehicle. It is further contemplated that controller 14 and the algorithm are capable of being modified to revise a location classification if later it is determined that the probability of consuming alcohol at that location has changed from an initial location classification.

Referring to FIG. 5, at step 110, controller 14 makes a determination as to whether the first location matches a location classification where the operator has a low probability of consuming alcohol. If the value of step 110 equals "yes," then the method proceeds to step 112. Otherwise, the method proceeds to step 114.

At step 112, controller 14 sets the low intoxication indication flag equal to "true" and stores the low intoxication indication flag in a memory. After step 112, the method proceeds to step 62.

At step 114, controller 14 makes a determination as to whether the first location matches a location classification where the operator has a medium probability of consuming alcohol. If the value of step 114 equals "yes," then the method proceeds to step 116. Otherwise, the method proceeds to step 120.

At step 116, controller 14 makes a determination as to whether the operator was intoxicated at the first location at a prior time. If the value of step 116 equals "yes," then the method proceeds to step 150. Otherwise, the method proceeds to step 118.

At step 118, controller 14 sets the low intoxication indication flag equal to "true" and stores the low intoxication indication flag in a memory. After step 118, the method proceeds to step 62.

At step 120, controller 14 makes a determination as to whether the first location matches a location classification where the operator has a high probability of consuming alcohol. If the value of step 120 equals "no," then the method proceeds to step 150. Otherwise, the method proceeds to step 122.

At step 122, controller 14 makes a determination as to whether the vehicle and the operator were at the first location less than a threshold time value. For example, were the vehicle and the operator at the first location less than ten minutes? If the value of step 110 equals "no," the method proceeds to step 124. Otherwise, the method proceeds to step 126.

At step 124, controller 14 sets the high intoxication indication flag equal to "true" and stores the high intoxication indication flag in a memory. After step 124, the method proceeds to step 58.

At step 126, controller 14 sets the medium intoxication indication flag equal to "true" and stores the medium intoxication indication flag in a memory and then the method proceeds to step 62. It is contemplated that in an alternative exemplary embodiment, the medium intoxication indication flag prompts controller 14 to gather additional data about the operator and/or signals from other sensors, for example from sensors that monitor vehicle operational parameters, before making a determination about the operator's cognitive ability to operate the vehicle.

Referring now to FIG. 6 and in an exemplary embodiment, controller 14 further makes a determination of an intoxication indication value in terms of a probability based on consideration of additional data. Additionally, controller 14 evaluates prior vehicle operational history and routines associated with the operator in making the determination as to whether the operator is intoxicated.

At step 150, controller 14 determines an intoxication indication value based on the first location, a calendar date, a time value indicative of a time of day, a time duration value indicative of the vehicle being at the first location, and historical data associated with the operator. In an exemplary embodiment, the intoxication indication value is expressed in terms of a probability value, as illustrated in steps 152 and 154. Controller 14 performs a set of instructions in determining whether the operator is intoxicated depending on the category of the intoxication indication value.

At step 152, controller 14 makes a determination as to whether the intoxication indication value is less than 0.25. If the value of step 152 equals "yes," the method proceeds to step 158. Otherwise, the method proceeds to step 154.

At step 158, controller 14 sets the low intoxication indication flag equal to "true" and stores the low intoxication indication flag in a memory. After step 158, the method proceeds to step 62.

At step 154, controller 14 makes a determination as to whether the intoxication indication value is greater than or equal to 0.25 and less than or equal to 0.75. If the value of step 154 equals "yes," the method proceeds to step 160. Otherwise, the method proceeds to step 166.

At step 160, controller 14 makes a determination as to whether the calendar date, time of day, first location, and time duration at first location fit a drinking routine of the operator. In an exemplary embodiment, the drinking routine of the operator includes any historical data such as prior arrests for intoxication, vehicle accidents related to the operator being intoxicated, prior calendar holidays where the operator was present at locations where alcohol is normally consumed, etc. If the value of step 160 equals "yes," the method proceeds to step 162. Otherwise, the method proceeds to step 164.

At step 162, controller 14 sets the medium intoxication indication flag equal to "true" and stores the medium intoxication indication flag in a memory. After step 162, the method proceeds to step 62.

At step 164, controller 14 sets the low intoxication indication flag equal to "true" and stores the low intoxication indication flag in a memory. After step 164, the method proceeds to step 62.

Referring again to step 154, when the value of step 154 equals "no," the method proceeds to step 166.

At step 166, controller 14 sets the high intoxication indication flag equal to "true" and stores the high intoxication indication flag in a memory. After step 166, the method proceeds to step 58.

Figure 7:
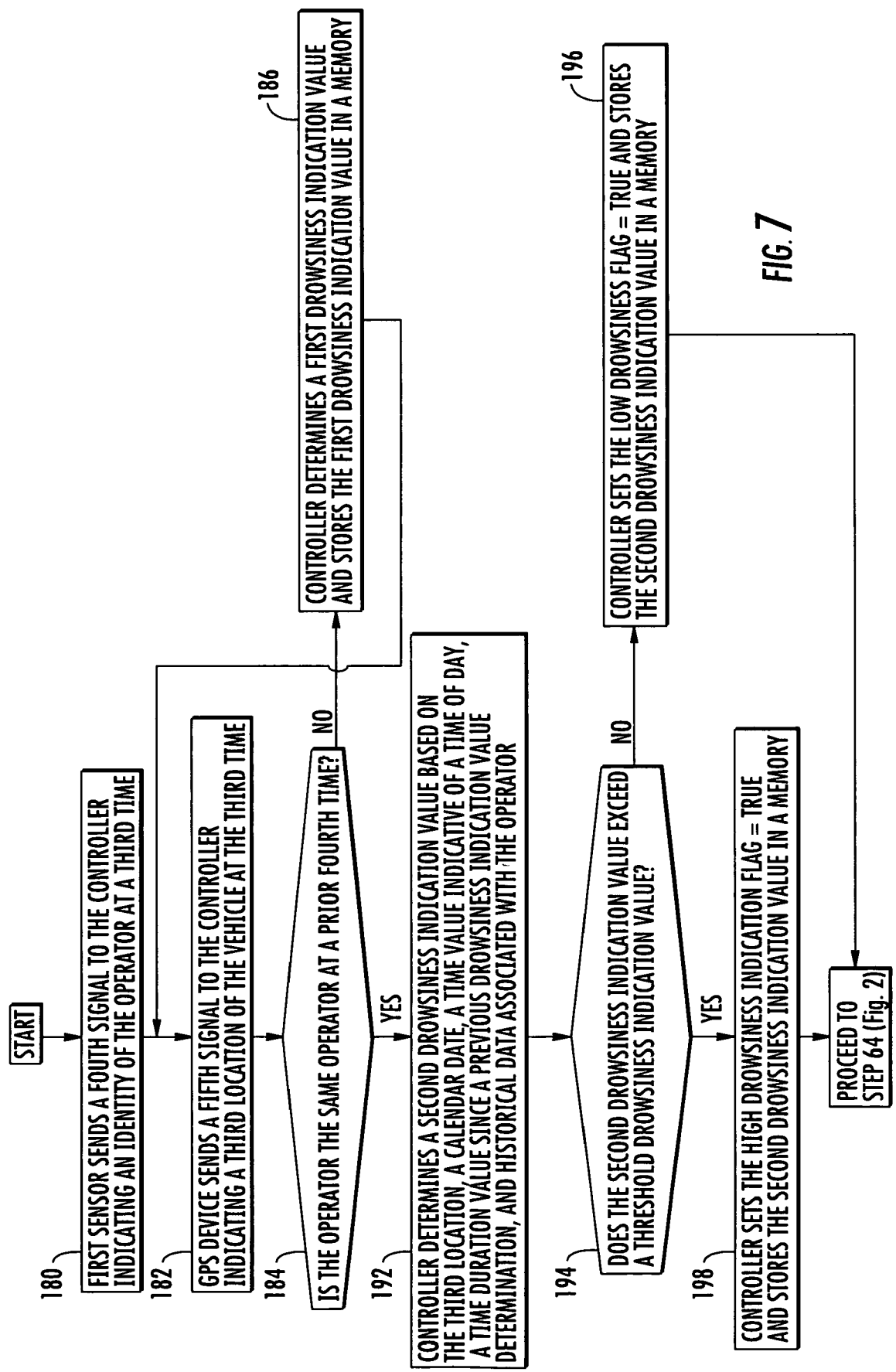

Referring now to FIG. 7, the drowsiness determination routine will be explained. The drowsiness determination routine determines a drowsiness indication value and compares that value to a threshold drowsiness indication value for evaluating whether the operator has sufficient rest to operate the vehicle.

At step 180, biometric sensor 16 sends a fourth signal to controller 14 indicating the identity of the operator at a third time.

At step 182, GPS device 18 sends a fifth signal to controller 14 indicating a third location of the vehicle at the third time.

At step 184, controller 14 makes a determination as to whether the operator was the same operator at a prior fourth time. If the value of step 184 equals "no," the method proceeds to step 186, because there is not sufficient prior data for consideration in the drowsiness determination routine. Otherwise, the method proceeds to step 192.

At step 186, controller 14 determines a first drowsiness indication value and stores the first drowsiness indication value in a memory. In an exemplary embodiment, the first drowsiness indication value is based on the third location, a calendar date and a time of day. After step 186, the method returns to step 182.

At step 192, controller 14 determines a second drowsiness indication value based on the third location, a calendar date, a time value indicative of a time of day, a time duration value since a previous drowsiness indication value determination, and historical data associated with the operator. In an exemplary embodiment, the historical data may include a drowsiness indication value determined at a previous time. Additionally and in an exemplary embodiment, the drowsiness determination routine utilizes vehicle location classifications for determining the drowsiness indication value.

In an exemplary embodiment and in the determination of the second drowsiness indication value at step 192, a previous sleep schedule of the operator is inferred from the vehicle location, an elapsed time that the vehicle remained at that location, a time that the operator leaves the location in the vehicle, and historical data associated with the operator. Estimation of the operator's previous sleep schedule includes a quantity of time the operator slept, times of day of sleep, and locations where the operator slept.

At step 194, controller 14 makes a determination as to whether the second drowsiness indication value exceeds a threshold drowsiness indication value. If the value of step 194 equals "no," the method proceeds to step 196. Otherwise, the method proceeds to step 198.

At step 196, controller 14 sets the low drowsiness indication flag equal to "true" and stores the second drowsiness indication value in a memory. After step 196, the method returns to step 64.

At step 198, controller 14 sets the high drowsiness indication flag equal to "true" and stores the second drowsiness indication value in a memory. After step 198, the method returns to step 64.

Figure 8:
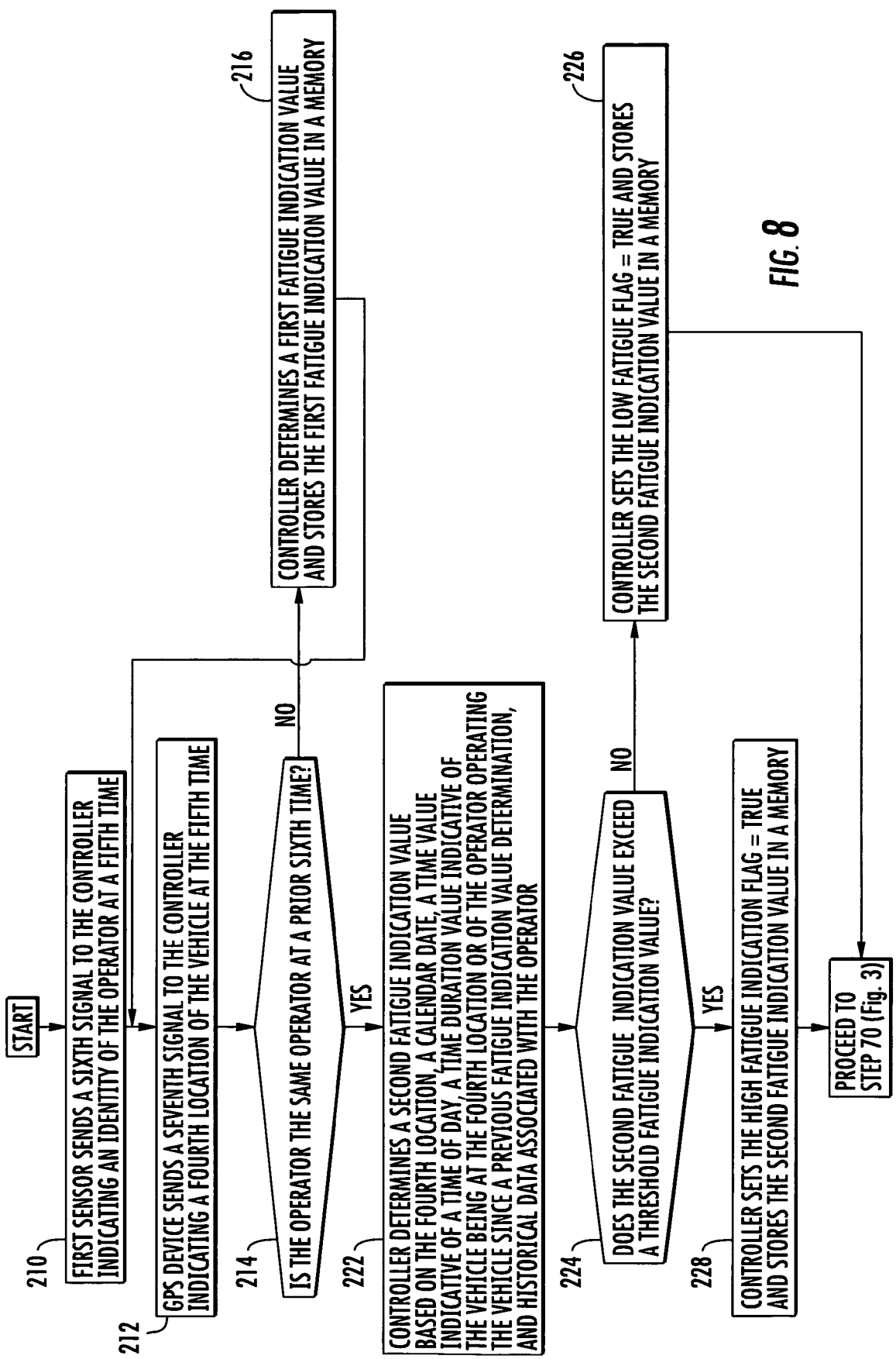

Referring now to FIG. 8, the fatigue determination routine will now be explained. The fatigue determination routine determines a fatigue indication value and compares that value to a threshold fatigue indication value for evaluating whether the operator is too fatigued to operate the vehicle.

At step 210, biometric sensor 16 sends a sixth signal to controller 14 indicating the identity of the operator at a fifth time.

At step 212, GPS device 18 sends a seventh signal to controller 14 indicating a fourth location of the vehicle at the fifth time.

At step 214, controller 14 makes a determination as to whether the operator was the same operator at a prior sixth time. If the value of step 214 equals "no," the method proceeds to step 216, because there is not sufficient prior data for consideration in the fatigue determination routine. Otherwise, the method proceeds to step 222.

At step 216, controller 14 determines a first fatigue indication value and stores the first fatigue indication value in a memory. After step 216, the method returns to step 212.

At step 222, controller 14 determines a second fatigue indication value based on the fourth location, a calendar date, a time value indicative of a time of day, a time duration value indicative of the vehicle being at the fourth location or an elapsed time of the operator operating the vehicle since a previous fatigue determination, and historical data associated with the operator. In an exemplary embodiment, the historical data includes a previous fatigue indication value. Additionally and in an exemplary embodiment, the fatigue determination routine utilizes vehicle location classifications for determining the fatigue indication value.

In an exemplary embodiment and in the determination of the second fatigue indication value at step 222, a previous work and driving schedule of the operator is inferred from the location, an elapsed time that the vehicle remained at that location, a time that the operator leaves the location in the vehicle, and historical data associated with the operator. Estimation of the operator's previous work and driving schedule includes elapsed times that the operator has worked and operated the vehicle, times of day that the operator worked and operated the vehicle, and routes along which the operator traveled in the vehicle.

At step 224, controller 14 makes a determination as to whether the second fatigue indication value exceeds a threshold fatigue indication value. If the value of step 224 equals "no," the method proceeds to step 226. Otherwise, the method proceeds to step 228.

At step 226, controller 14 sets the low fatigue indication flag equal to "true" and stores the second fatigue indication value in a memory. After step 226, the method returns to step 70.

At step 228, controller 14 sets the high fatigue indication flag equal to "true" and stores the second fatigue indication value in a memory. After step 228, the method returns to step 70.

Figure 9:
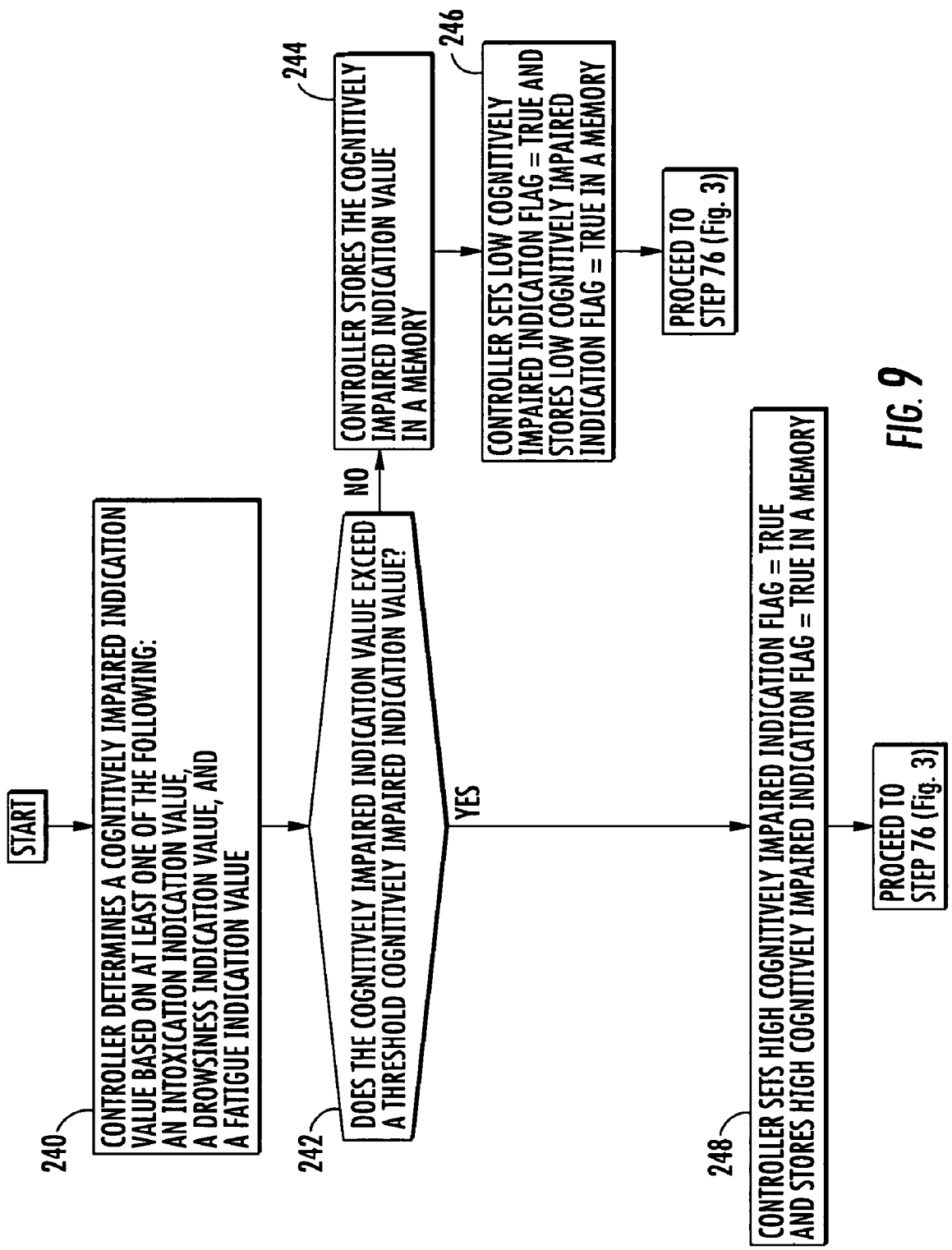

Referring now to FIG. 9, the cognitively impaired determination routine will now be explained. The cognitively impaired determination routine determines a cognitively impaired state of the operator based on at least one of the intoxication indication value, the drowsiness indication value, and the fatigue indication value. The cognitively impaired determination routine is configured to account for scenarios where controller 14 determines that the operator has a level of intoxication, drowsiness or fatigue that raises concerns about the operator's cognitive ability to safely operate the vehicle even though the level of intoxication, drowsiness or fatigue has not exceeded a threshold level. The cognitively impaired determination routine is also configured to account for a scenario where any two or three of intoxication level, drowsiness level, and fatigue level raises concerns about the operator's cognitive ability to operate the vehicle even though each level of intoxication, drowsiness or fatigue has not exceeded a threshold level.

At step 240, controller 14 determines a cognitively impaired indication value based on at least one of the following: an intoxication indication value, a drowsiness indication value, and a fatigue indication value.

At step 242, controller 14 makes a determination as to whether the cognitively impaired indication value exceeds a threshold cognitively impaired indication value. If the value of step 242 equals "no," the method proceeds to step 244. Otherwise, the method proceeds to step 248.

At step 244, controller 14 stores the cognitively impaired indication value in a memory. After step 244, the method proceeds to step 246.

At step 246, controller 14 sets the low cognitively impaired indication flag equal to "true" and stores the low cognitively impaired indication flag in a memory. After step 246, the method proceeds to step 76.

At step 248, controller 14 sets the high cognitively impaired indication flag equal to "true" and stores the high cognitively impaired indication flag in a memory. After step 248, the method proceeds to step 76.

As described above, the methods for determining whether a vehicle operator has an impaired cognitive state can be at least partially embodied in the form of computer-implemented processes and apparatuses for practicing those processes. In the exemplary embodiments, the methods or algorithms are embodied in computer program code executed by one or more controllers. The present methods may be embodied in the form of computer program code containing instructions embodied in one or more computer-readable mediums such as floppy diskettes, CD-ROMS, hard drives, flash memory, or the like, wherein, when the computer program code is loaded into and executed by a controller, the controller becomes an apparatus for practicing the invention.

The exemplary embodiments of the operator cognitive state estimating system and method of use disclosed herein determine whether a vehicle operator has an impaired cognitive state, wherein the determination is made with minimal participation of the operator and minimal intrusion on the operator's freedom to operate the vehicle.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the present application.

What is claimed is:

1. A method for determining whether an operator of a vehicle is intoxicated, comprising:
generating a first signal indicative of a first location of the vehicle at a first time, utilizing a global positioning system device, when a vehicle ignition switch is in a predetermined operating position;
determining a location classification associated with the first location of the vehicle based on the first signal, utilizing a controller;
determining whether the operator is intoxicated based on the location classification and a time duration value indicative of the vehicle being at the first location, utilizing the controller; and
generating a second signal when the operator is intoxicated, utilizing the controller.

2. The method as in claim 1, wherein determining whether the operator is intoxicated is further based on a calendar date and historical data associated with the operator.

3. The method as in claim 1, wherein determining whether the operator is intoxicated is further based on a probability of the operator consuming alcohol at the first location.

4. The method as in claim 1, further comprising generating an identity signal indicative of an identity of the operator, utilizing a biometric sensor, when the ignition switch is in the predetermined operating position.

5. The method as in claim 1, further comprising generating a blood alcohol content value, utilizing a first sensor operably communicating with the controller, and if the blood alcohol content value is greater than or equal to a threshold blood alcohol content value, then generating an excessive blood alcohol level signal indicating the operator is intoxicated, utilizing the controller.

6. The method as in claim 1, further comprising:
determining whether the operator was intoxicated at a prior location at a second time, utilizing the controller; and
if an elapsed time interval between the first time and the second time is less than a threshold time interval, then generating a third signal indicating the operator is intoxicated, utilizing the controller.

7. The method as in claim 1, further comprising determining an intoxication indication value based on the first signal, a calendar date, a time value indicative of a time of day, a time duration value indicative of the vehicle being at the first location, and historical data associated with the operator and if the intoxication indication value is greater than a threshold intoxication indication value, then generating a fourth signal indicating the operator is intoxicated, utilizing the controller.

8. The method as in claim 7, wherein the intoxication indication value is a probability value in a predetermined range.

9. The method as in claim 1, further comprising inducing a light-emitting diode to emit light indicating the operator is intoxicated, utilizing the second signal.

10. A system for determining whether an operator of a vehicle is intoxicated, comprising:
a global positioning system device configured to generate a first signal indicative of a location of the vehicle at a first time, when a vehicle ignition switch is in a predetermined operating position; and
a controller operably communicating with the global positioning system device, the controller configured to determine whether the operator is intoxicated based on a location classification associated with the location of the vehicle based on the first signal and a time duration value indicative of the vehicle being at the location, the controller further configured to generate a second signal when the operator is intoxicated.

11. The system as in claim 10, wherein the controller is further configured to determine whether the operator is intoxicated based on a calendar date and historical data associated with the operator.

12. The system as in claim 10, further comprising a biometric sensor configured to generate an identity signal indicative of an identity of the operator, when the ignition switch is in the predetermined operating position.

13. The system as in claim 12, wherein the biometric sensor comprises a fingerprint sensor.

14. The system as in claim 10, further comprising a first sensor operably communicating with the controller, the first sensor configured to generate a third signal indicative of a breath-alcohol content value associated with the operator, the controller further configured to generate a fourth signal indicating the operator is intoxicated at the first time if the breath-alcohol content value is greater than or equal to a threshold breath-alcohol content value.

15. A method for determining whether an operator of a vehicle is drowsy, comprising:
generating a first signal indicative of a first location of the vehicle at a first time, utilizing a global positioning system device, when a vehicle ignition switch is in a predetermined operating position;
determining a drowsiness indication value utilizing a controller based on the first signal and a time duration value indicative of the vehicle being at the first location; and
if the drowsiness indication value is greater than a threshold drowsiness indication value, then generating a second signal indicating that the operator is drowsy at the first time, utilizing the controller.

16. The method as in claim 15, wherein determining the drowsiness indication value is further based on a calendar date and historical data associated with the operator.

17. The method as in claim 15, wherein determining the drowsiness indication value is further based on a classification associated with the first location.

18. The method as in claim 15, further comprising generating an identity signal indicative of an identity of the operator, utilizing a biometric sensor, when the ignition switch is in the predetermined operating position.

19. The method as in claim 15, further comprising determining a second drowsiness indication value based on the first signal, a time value indicative of a time of day, a time duration value since a previous drowsiness determination, and historical data associated with the operator, if the operator was operating the vehicle at a second time prior to the first time, utilizing the controller.

20. The method as in claim 19, further comprising generating a third signal indicating that the operator is drowsy, utilizing the controller, if the second drowsiness indication value is greater than the threshold drowsiness indication value.

21. The method as in claim 15, further comprising inducing a light-emitting diode to emit light indicating the operator is drowsy, utilizing the second signal.

22. A system for determining whether an operator of a vehicle is drowsy, comprising:
 a global positioning system device configured to generate a first signal indicative of a location of the vehicle at a first time, when a vehicle ignition switch is in a predetermined operating position; and
 a controller operably communicating with the global positioning system device, the controller configured to determine a drowsiness indication value based on the first signal and a time duration value indicative of the vehicle being at the location, the controller further configured to generate a second signal indicating that the operator is drowsy at the first time if the drowsiness indication value is greater than a threshold drowsiness indication value.

23. The system as in claim 22, wherein the controller is further configured to determine the drowsiness indication value based on a calendar date and historical data associated with the operator.

24. The system as in claim 22, further comprising a biometric sensor configured to generate an identity signal indicative of an identity of the operator.

25. A method for determining whether an operator of a vehicle is fatigued, comprising:
 generating a first signal indicative of a first location of the vehicle at a first time, utilizing a global positioning system device, when a vehicle ignition switch is in a predetermined operating position;
 determining a fatigue indication value utilizing a controller based on the first signal and a time duration value indicative of the vehicle being at the first location; and
 if the fatigue indication value is greater than a threshold fatigue indication value, then generating a second signal indicating that the operator is fatigued at the first time, utilizing the controller.

26. The method as in claim 25, wherein determining the fatigue indication value is further based on a calendar date and historical data associated with the operator.

27. The method as in claim 25, wherein determining the fatigue indication value is further based on a classification associated with the first location.

28. The method as in claim 25, further comprising generating an identity signal indicative of an identity of the operator, utilizing a biometric sensor, when the ignition switch is in the predetermined operating position.

29. The method as in claim 25, further comprising determining a second fatigue indication value based on the first signal, a time value indicative of a time of day, a time duration value indicative of the vehicle being at the first location or an elapsed time of the operator operating the vehicle since a previous fatigue indication value determination, and historical data associated with the operator, if the operator was operating the vehicle at a second time prior to the first time, utilizing the controller.

30. The method as in claim 29, further comprising generating a third signal indicating that the operator is fatigued, utilizing the controller, if the second fatigue indication value is greater than the threshold fatigue indication value.

31. The method as in claim 25, further comprising inducing a light-emitting diode to emit light indicating the operator is fatigued, utilizing the second signal.

32. A system for determining whether an operator of a vehicle is fatigued, comprising:
 a global positioning system device configured to generate a first signal indicative of a location of the vehicle at a first time, when a vehicle ignition switch is in a predetermined operating position; and
 a controller operably communicating with the global positioning system device, the controller configured to determine a fatigue indication value based on the first signal and a time duration value indicative of the vehicle being at the location, the controller further configured to generate a second signal indicating that the operator is fatigued at the first time if the fatigue indication value is greater than a threshold fatigue indication value.

33. The system as in claim 32, wherein the controller is further configured to determine the fatigue indication value based on a calendar date and historical data associated with the operator.

34. The system as in claim 32, further comprising a biometric sensor configured to generate an identity signal indicative of an identity of the operator.

35. A method for determining whether an operator of a vehicle has an impaired cognitive state, comprising:
 determining an intoxication indication value indicative of whether the operator is intoxicated, utilizing a controller;
 determining a drowsiness indication value indicative of whether the operator is drowsy, utilizing the controller;
 determining a fatigue indication value indicative of whether the operator is fatigued, utilizing the controller; and
 determining a cognitively impaired indication value based on at least one of the intoxication indication value, the drowsiness indication value, and the fatigue indication value; and
 if the cognitively impaired indication value is greater than a threshold cognitively impaired indication value, then generating a signal indicating that the operator is cognitively impaired, utilizing the controller.

36. The method as in claim 35, further comprising inducing a light-emitting diode to emit light indicating the operator is cognitively impaired, utilizing the signal.

37. A system for determining whether an operator of a vehicle has an impaired cognitive state, comprising:
 a controller configured to determine a cognitively impaired indication value based on at least one of an intoxication indication value, a drowsiness indication value, and a fatigue indication value, the controller further configured to generate a signal indicating that the operator is cognitively impaired if the cognitively impaired indication value is greater than a threshold cognitively impaired indication value.

* * * * *